US005800983A

United States Patent [19]
Bridon et al.

[11] Patent Number: 5,800,983
[45] Date of Patent: Sep. 1, 1998

[54] PEPTIDES FOR HIV-1 DETECTION

[75] Inventors: Dominique P. Bridon, Morton Grove; Isaac S.-Y. Sze, deceased, late of Gurnee, by Carolina Luiz, Loch-Hung Leo Sze, Leah Samantha Sze, heirs; David J. Daghfal, Aurora, all of Ill.; Keeve D. Jaffe, Trevor, Wis.; Tracey L. Colpitts, Round Lake, Ill.

[73] Assignee: Abbott Laboratories, Abbott Park, Ill.

[21] Appl. No.: 837,732

[22] Filed: Apr. 22, 1997

Related U.S. Application Data

[63] Continuation of Ser. No. 472,597, Jun. 7, 1995, abandoned.

[51] Int. Cl.$^6$ ..................................................... C12Q 1/70
[52] U.S. Cl. .................. 435/5; 435/7.1; 435/7.2; 435/7.25; 435/7.9; 435/7.92; 435/7.94; 435/974; 435/975; 436/518; 436/519; 436/520; 436/521; 436/526; 436/528; 436/530; 436/533; 530/326; 530/806; 530/812; 530/826
[58] Field of Search .................. 435/5, 7.1, 7.2, 435/7.25, 7.72, 7.9, 7.92, 7.93, 7.94, 7.95, 974, 975; 436/518–521, 526, 528–534; 530/326, 806, 812, 826

[56] References Cited

U.S. PATENT DOCUMENTS

| | | | |
|---|---|---|---|
| 5,075,077 | 12/1991 | Durley, III et al. | 422/56 |
| 5,304,466 | 4/1994 | De Leys et al. | 435/5 |
| 5,320,808 | 6/1994 | Holen et al. | 422/64 |
| 5,374,518 | 12/1994 | Hunt et al. | 435/5 |

FOREIGN PATENT DOCUMENTS

| | | |
|---|---|---|
| 0424634 | 5/1991 | European Pat. Off. |
| 0425633 | 5/1991 | European Pat. Off. |
| 0591914 | 4/1994 | European Pat. Off. |
| 0727483 | 8/1996 | European Pat. Off. |
| 4405810 | 8/1995 | Germany |
| 9007119 | 6/1990 | WIPO |

OTHER PUBLICATIONS

W. Janssens et al., "Genetic and Phylofenetic Analysis of env Subtypes G and H in Central Africa", *AIDS Research And Human Retroviruses*, vol. 10, No.7, (1990), pp. 877–879.

N.R. Rose et al., "Immunoassay by Particle Counting", *Manual Of Clinical Laboratory Immunology*, 3rd edition, Chapter 8, (1996), pp. 43–48.

R. De Leys et al., "Isolation and Partial Characterzation of an Unusual Human Immunodeficiency Retrovirus from Two Persons of West-Central African Origin", *Journal Of Virology*, vol. 64, No. 3, (1990), pp. 1207–1216.

J.W. Gnaan, Jr. et al., "Synthetic Peptide Immunoassay Distinguishes HIV Type 1 and HIV Type 2 Infections", *Science*, vol. 237, (1987), pp. 1346–1349.

J.C. Hunt et al., "Discrimination Between HIV-1 and HIV-2 Seropositive Individuals Using Mouse Monoclonal Antibodies Directed to HIV Transmembrane Proteins", *AIDS Research And Human Retroviruses*, vol. 6, No. 7, (1990), pp. 883–898.

M.C. Cot et al., "Dual HIV-1 and HIV-2 Infection in West Africa Supported by Synthetic Peptide Analysis", *AIDS Research And Human Retroviruses*, vol 4, (1988), pp. 239–241.

L.G. Gurtler et al., "A New Subtype of Human Immunodeficiency Virus Type 1 (MVP-5180) from Cameroon", *Journal Of Virology*, vol. 68, No. 3, (1994), pp. 1581–1585.

I. Loussert-Ajaka et al., "HIV-1/HIV-2 Seronegativity in HIV-1 Subtype O Infected Patients", *The Lancet*, vol. 343, (1994), pp. 1393–1394.

M. Vanden Haesevelde et al., "Genomic Cloning and Complete Sequence Analysis of a Highly Divergent African Human Immunodeficiency Virus Isolate", *Journal Of Virology*, vol. 68, No. 3, (1994), pp. 1586–1596.

P. Charneau et al., "Isolation and Envelope Sequence of a Highly Divergent HIV-1 Isolate: Definition of a New HIV-1 Group", *Virology*, vol. 205, (1994), pp. 247–253.

Meyers et al., *Human Retroviruses And Acids 1993: A Compilation And Analysis Of Nucleic Acid And Sequences*, (Los Alamos National Laboratory, Los Alamos, NM), (1993).

*Primary Examiner*—Jeffrey Stucker
*Attorney, Agent, or Firm*—Andreas M. Danckers

[57] ABSTRACT

HIV-1 peptides having at least one point mutation between position 593 and 611 of the HIV-1 gp160 amino acid sequence. The point mutation either is at position 604 or 610, or both positions. Immunoassays which utilize these peptides are provided, as well as, diagnostic test kits which contain these peptides.

21 Claims, 5 Drawing Sheets

PEPTIDES FOR HIV-1 DETECTION

This application is a continuation of U.S. Ser. No. 08/472597, filed Jun. 7, 1995, now abandoned.

BACKGROUND OF THE INVENTION

This invention relates generally to peptides useful for detecting HIV-1 antibody, and more particularly, relates to the detection of HIV-1 subtype O antibodies by utilizing an amino acid sequence of HIV-1 gp41 immunodominant region (IDR) which contains two point mutations, one at position 604 and one at position 610 of the HIV-1 subtype B gp160 sequence (the numbering is according to HIV-1 strain LAI published in Myers et al., infra).

Currently there are six recognized subtypes (so-called "clades") of HIV-1 designated as A, B, C, D, E, and F as described in Myers et al., Human Retroviruses and AIDS 1993: A Compilation and Analysis of Nucleic Acid and Amino Acid Sequences (Los Alamos National Laboratory, Los Alamos, N. Mex.) (1993). Recently, additional subtypes G and H have been described. See, for example, Janssens et al., AIDS Research and Human Retroviruses 10: 877 (1994); and Myers et al., supra. Of emerging particular importance is the recognition of a markedly divergent group of HIV-1 sequences designated as "O". HIV-1 subtype O was first described in 1987, and was termed "O" for "outlier" because it was found to have only about 50% sequence identity at the nucleic acid level of the env gene with the other subtypes of HIV-1. These other subtypes, noted above, contain about 75% sequence identity at the nucleic acid level of the env gene with one another. The earliest reports on the sequence of O type viruses indicated that on the phylogenetic tree, SIVCPZGAB lies closer to the other HIV-1 than does group-O; i.e. this chimpanzee virus sits between group-M and group-O. See, for example, Gürtler et al., J. Virology 68: 1581–1585 (1994); Vanden Haesevelde et al., J. Virology 68: 1586–1596 (1994); De Leys et al., J. Virology 64: 1207–1216 (1990); De Leys et al., U.S. Pat. No. 5,304,466; Gürtler et al., European Patent Publication No. 0591914A2. The group O sequences are the most divergent of the HIV-1 sequences described to date, while subtype B is the most common subtype of HIV-1.

HIV serology has been characterized in large part by the amino acid sequences of the expressed viral proteins (antigens), particularly those comprising the core and envelope. Antigens which are structurally and functionally similar but have different amino acid sequences elicit antibodies which may be similar but not identical in their specificity for antigen. One example is the antigenic difference between HIV-1 and HIV-2 gp41 IDR, which can be exploited in a variety of ways to serologically discriminate between individuals exposed to HIV-1 and/or HIV-2. See, for example, Hunt et al., AIDS Research and Human Retroviruses 6:883–898 (1990); Gnaan et al., Science 237:1346–1349 (1987); Cot et al., AIDS Research and Human Retroviruses 4:239–241 (1988); Hunt et al., U.S. Pat. No. 5,374,518. Similarly, HIV-1 group O viruses are antigenically and serologically distinguishable from other HIV-1 subtypes. Loussert-Ajaka et al., The Lancet 343: 1393–1394 (1994); Gürtler et al., J. Virology 68: 1581–1585 (1994); Vanden Haesevelde et al., J. Virology 68: 1586–1596 (1994); De Leys et al., J. Virology 64 (supra); U.S. Pat. No. 5,304,466; Gürtler et al., E. P. O. Publication 0591914A2.

The ability to detect HIV-1 subtype O has become a critical concern in the blood bank community. In one study, it was reported that commercial assays capable of detecting HIV-1 subtype B were not able to detect a panel of 9 samples positive for HIV-1 subtype O (I. Loussert-Ajaka et al., The Lancet 343:1393–1394 (1994)). Although the number of actual confirmed cases of infection due to HIV-1 subtype O is limited in number and geographically, there are indications that this subtype is beginning to spread from Cameroon, the initial site of the virus, to neighboring countries, such as Equatorial Guinea.

It would be advantageous to provide a reagent which could be used in an assay to detect the presence of HIV-1 subtype O antibodies in test samples.

SUMMARY OF THE INVENTION

The present invention provides a polypeptide having a point mutation in the HIV-1 sub-type B IDR at position 604. More specifically, the polypeptide point at position 604 is a lysine (K). The polypeptide is identified by SEQUENCE I.D. No. 2. The present invention also provides a polypeptide having a point mutation in the HIV-1 sub-type B IDR at position 610. More specifically, the polypeptide point at position 610 is a tyrosine (Y). The polypeptide is identified by SEQUENCE I.D. No. 3. A polypeptide having two single point mutations in the HIV-1 sub-type B IDR at positions 604 and 610 also is provided. The polypeptide said point mutation at position 604 is a lysine (K) and the point mutation at position 610 is a tyrosine (Y). The polypeptide is identified by SEQUENCE I.D. No. 4.

The present invention provides an immunoassay to detect the presence of HIV antibodies contacting said test sample with a solid phase to which has been attached an HIV-1 polypeptide having a point mutation between positions 593 and 611 and incubating for a time and for conditions sufficient to form polypeptide/antibody complexes; contacting said polypeptide/antibody complexes with an incubator reagent comprising a member of a specific binding pair of HIV antibody attached to a signal generating compound capable of generating a measurable signal and incubating for a time and for conditions sufficient to form polypeptide/antibody/indicator reagent complexes; determing the presence of HIV antibodies by detecting the measurable signal. The point mutation is at position 604, or position 610. Or, the point mutations are at positions 604 and 610. The solid phase is selected from the group consisting of the walls of wells of a reaction tray, test tubes, polystyrene beads, magnetic beads, nitrocellulose strips, membranes, microparticles such as latex particles, sheep (or other animal) red blood cells and DURACYTES™ (fixed erythrocytes). The signal generating compound of the indicator reagent is selected from the group consisting of chromogens, enzymes, luminescent compounds, chemiluminescent compounds, radioactive elements, and direct visual labels. The specific binding pair member of said indicator reagent preferably is anti-human IgG.

The present invention provides an improved immunoassay for detecting HIV antibody in a test sample comprising contacting said test sample with an HIV-1 polypeptide and detecting the presence of said antibody wherein the improvement comprises using or utilizing a polypeptide having a point mutation between positions 593 and 611 of the HIV-1 gp160 sequence.

Also provided is a dignostic test kit capable of detecting HIV antibodies, wherein said kit comprises a container containing a polypeptide having a sequence selected from the group consisting of SEQUENCE I.D. No. 2, SEQUENCE I.D. No. 3 and SEQUENCE I.D. No. 4.

DETAILED DESCRIPTION O sheep (or other animal) red blood cells, duracytes and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, DURACYTES™ (fix erythrocytes), and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. These materials may be used in suitable shapes, such as films, sheets, or plates, or they may be coated onto or bonded or laminated to appropriate inert carriers, such as paper, glass, plastic films, or fabrics.

Other embodiments which utilize various other solid phases also are contemplated and are within the scope of this invention. For example, ion capture procedures for immobilizing an immobilizable reaction complex with a negatively charged polymer, described in U.S. patent application Ser. No. 150,278, now abandoned, corresponding to EP publication 0326100 and U.S. patent application Ser. No. 375,029 U.S. Pat. No. 5,459,078, (EP publication no. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemilumninescent signal measurements as described in U.S. patent application Ser. No. 921,979, U.S. Pat. No. 5,468,646, corresponding to EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in U.S. patent application Ser. No. 425,651, U.S. Pat. No. 5,244,630, and Ser. No. 425,643, U.S. Pat. No. 5,089,424, which correspond to published EPO applications Nos. EP 0 425 633 and EP 0 424 634, respectively.

The use of scanning probe microscopy (SPM) for immunoassays also is a technology to which the peptides of the present invention are easily adaptable. In scanning probe microscopy, in particular in atomic force microscopy, the capture phase, for example, at least one of the peptides disclosed herein, is adhered to a solid phase, a test sample suspected of containing the antibody of interest is contacted with the solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in U.S. patent application Ser. No. 662,147, now abandoned. The use of SPM to monitor specific binding reactions can occur in many ways. In one way, one member of a specific binding partner (analyte specific substance which is a peptide disclosed herein) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art. Also, polyelectrolyte interactions may be used to immobilize a specific binding partner on a surface of a test piece by using techniques and chemistries described by pending U.S. patent application Ser. No. 150,278, filed Jan. 29, 1988, and Ser. No. 375,029, filed Jul. 7, 1989. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not thought to alter the specific binding properties of the test piece.

It is contemplated that the reagents employed for the assay can be provided in the form of a test kit with one or more containers such as vials or bottles, with each container containing a separate reagent such as a peptide, or a mixture of peptides, or an indicator reagent when employed in the assay. Other components such as buffers, controls, and the like, known to those of ordinary skill in art, may be included in such test kits.

Assay formats can be designed which utilize the peptides detailed herein, including as antigens in immunoassays, immunogens for antibody production, and the like. In an assay format to detect the presence of antibody against a specific analyte (for example, HIV-1) in a human test sample, the human test sample is contacted and incubated with a solid phase coated with at least one HIV-1 peptide disclosed herein. If antibodies specific for the analyte are present in the test sample, they will form a complex with the peptide and become affixed to the solid phase. After the complex has formed, unbound materials and reagents are removed by washing the solid phase. These complexes then are contacted with and reacted with an indicator reagent and allowed to incubate for a time and under conditions for second complexes to form. The presence of antibody in the test sample to the peptide is determined by detecting the signal generated. Signal generated above a cut-off value is indicative of antibody to the analyte present in the test sample. With many indicator reagents, such as enzymes, the amount of antibody present is proportional to the signal generated. Depending upon the type of test sample, the test sample may be diluted with a suitable buffer reagent, concentrated or contacted with the solid phase without any manipulation ("neat"). For example, it usually is preferred to assay serum or plasma samples which previously have been diluted, or concentrate specimens such as urine, in order to determine the presence and/or amount of antibody present.

In addition, more than one peptide can be used in the assay format just described to test for the presence of antibody against a specific infectious agent by utilizing peptides against various antigenic epitopes of the viral genome of the infectious agent under study. Thus, it may be preferred to use peptides which contain epitopes within a specific viral antigenic region as well as epitopes from other antigenic regions from the viral genome to provide assays which have increased sensitivity and perhaps greater specificity than using a peptide from one epitope. Such an assay can be utilized as a confirmatory assay. In this particular assay format, a known amount of test sample is contacted with known amount(s) of at least one solid support coated with at least one peptide disclosed herein for a time and under conditions sufficient to form peptide/antibody complexes. These complexes then are contacted with known amount(s) of appropriate indicator reagent(s) for a time and under suitable conditions for a reaction to occur. A signal is generated and this resultant signal is compared to a negative test sample in order to determine the presence of antibody to the analyte in the test sample. It further is contemplated that, when using certain solid phases such as microparticles, each peptide utilized in the assay can be attached to a separate microparticle, and a mixture of these microparticles can be made by combining the various coated microparticles, which can be optimized for each assay.

Variations to the above-described assay formats include the incorporation of at least one of the synthetic peptides disclosed herein as well as recombinant proteins or synthetic peptides specific to different analytes, attached to the same or to different solid phases for the detection of the presence of antibody to either analyte (for example, a synthetic peptide disclosed herein specific for certain antigenic regions of HIV-1 coated on the same or different solid phase with recombinant proteins specific for certain antigenic region(s) of a different infective agent, to detect the presence of either (or both) infective agents.

In yet another assay format, peptides containing antigenic epitopes are useful in competitive assays such as neutralization assays. To perform a neutralization assay, a peptide representing an epitope of an antigenic region of HIV-1, is solubilized and mixed with a sample diluent to a final concentration of between 0.5 to 50.0 µg/ml. A known amount of test sample (for example, 10 µl), either diluted or non-diluted, is added to a reaction well, followed by, for example, 400 µl of the sample diluent containing a peptide disclosed herein. If desired, the mixture may be preincubated for approximately 15 minutes to two hours. A solid phase coated with the peptide described herein then is added to the reaction well, and incubated for one hour at approximately 40° C. After washing, a known amount of an indicator reagent, for example, 200 µl of a peroxidase labelled goat anti-human IgG in a conjugate diluent, is added and incubated for about one hour at 40° C. After washing and when using an enzyme conjugate such as described, an enzyme substrate, for example, OPD substrate, is added to the mixture and incubated at room temperature for thirty minutes. The reaction is terminated by adding a stopping reagent such as 1N sulfuric acid to the reaction well. Absorbance is read at 492 nm. Test samples which contain antibody to the specific peptide generate a reduced signal caused by the competitive binding of the peptides to these antibodies in solution. The percentage of competitive binding may be calculated by comparing absorbance value of the sample in the presence of peptide to the absorbance value of the sample assayed in the absence of a peptide at the same dilution. Thus, the difference in the signals generated between the sample in the presence of peptide and the test sample in the absence of peptide is the measurement used to determine the presence or absence of antibody.

In another assay format, the peptides of the invention can be used in immunodot blot assay systems. The immunodot blot assay system uses a panel of purified recombinant polypeptides or synthetic peptides placed in an array on a nitrocellulose solid support. The prepared solid support is contacted with a test sample and captures specific antibodies (specific binding member) to the recombinant protein and/or synthetic peptides (other specific binding member) to form specific binding member pairs. The captured antibodies are detected by reaction with an indicator reagent. Preferably, the conjugate specific reaction is quantified using a reflectance optics assembly within an instrument which has been described in U.S. patent application Ser. No. 07/227,408 filed Aug. 2, 1988 now abandoned. The related U.S. patent application Ser. No. 07/227,586, U.S. Pat. No. 5,311,426, and Ser. No. 07/227,590 U.S. Pat. No. 5,311,426, (both of which were filed on Aug. 2, 1988) further described specific methods and apparatus useful to perform an immunodot blot assay, as well as U.S. Pat. No. 5,075,077, which enjoys common ownership and is incorporated herein by reference. Briefly, a nitrocellulose-base test cartridge is treated with multiple antigenic peptides. Each peptide is contained within a specific reaction zone on the test cartridge. After all the antigenic polypeptides have been placed on the nitrocellulose, excess binding sites on the nitrocellulose are blocked. The test cartridge then is contacted with a test sample such that each antigenic peptide in each reaction zone will react if the test sample contains the appropriate antibody. After reaction, the test cartridge is washed and any antigen-antibody reactions are identified using suitable well-known reagents. As described in the patents and patent applications listed herein, the entire process is amenable to automation. The specifications of these applications related to the method and apparatus for performing an immunodot blot assay are incorporated herein by reference.

The peptides disclosed herein can be used in assays which employ a first and second solid support, as follows, for detecting antibody to a specific antigen of an analyte in a test sample. In this assay format, a first aliquot of a test sample is contacted with a first solid support coated with a first peptide specific for an analyte for a time and under conditions sufficient to form peptide/analyte antibody complexes. Then, these complexes are contacted with an indicator reagent specific for the peptide. The signal generated from the indicator reagent is detected to determine the presence, if any, of antibody to the peptide present in the test sample. Following this, the presence of a different antigenic determinant of the same analyte is determined by contacting a second aliquot of a test sample with a second solid support coated with a synthetic peptide or recombinant protein for the second antibody for a time and under conditions sufficient to form recombinant protein or synthetic peptide/ second antibody complexes. The complexes are contacted with a second indicator reagent specific for the antibody of the complex. The signal generated from the indicator reagent is detected in order to determine the presence of antibody in the test sample, wherein the presence of antibody to either analyte, or both, indicates the presence of anti-analyte in the test sample. It also is contemplated that the solid supports can be tested simultaneously.

Haptens may be used to enhance the signal generated, and thus the sensitivity of the assay. The use of haptens is known in the art. It is contemplated that haptens also can be used in assays employing the peptides disclosed herein in order to enhance performance of the assay.

Another assay method for the detection of antibody in a test sample according to the present invention includes flow cytometric procedures and particle counting procedures. For example, in particle counting, analytes which are antibody members of specific binding pairs are quantified by mixing an aliquot of test sample suspected of containing a specific antibody with microparticles coated with a capture reagent specific for such antibody such as at least one of the peptides disclosed herein, capable of binding to the antibody of interest as the other member of the specific binding pair. If the antibody is present in the test sample, it will bind to some of the microparticles coated with the capture reagent and agglutinates will form. The analyte concentration is inversely proportional to the unagglutinated particle count. See, for example, Rose et al., eds., *Manual of Clinical Laboratory Immunology*, 3rd edition, Chapter 8, pages 43–48, American Society for Microbiology, Washington, D.C. (1986).

Flow cytometry methods that sense electronic and optical signals from cells or particles which are illuminated allows determination of cell surface characteristics, volume and cell size. Antibody present in, for example, a test sample are bound to a peptide disclosed herein and detected with a fluorescent dye which is either directly conjugated to the peptide or added via a second reaction. Different dyes, which may be excitable at different wavelengths, can be used with more than one peptide specific to different analytes such that more than one analyte can be detected from one sample. In fluorescence flow cytometry, a suspension of particles, typically cells in a test sample, is transported through a flowcell where the individual particles in the sample are illuminated with one or more focused light beams. One or more detectors detect the interaction between the light beam(s) and the labeled particles flowing through the flowcell. Commonly, some of the detectors are designed to measure fluorescence emissions, while other detectors measure scatter intensity or pulse duration. Thus, each particle that passes through the flowcell can be mapped into a feature space whose axes are the emission colors, light intensities, or other properties, i.e., scatter, measured by the detectors. In one situation, the different particles in the sample map into distinct and non-overlapping regions of the feature space, allowing each particle to be analyzed based on its mapping in the feature space. To prepare a test sample for flow cytometry analysis, the operator manually pipettes a volume of test sample from the sample tube into an analysis tube. A volume of the desired fluorochrome labeled peptide is added. The sample/peptide mixture then is incubated for a time and under conditions sufficient to allow antibody/peptide bindings to take place. After incubation, and if necessary, the operator adds a volume of RNS lyse to destroy any RBC's in the sample. After lysis, the sample is centrifuged and washed to remove any left-over debris from the lysing step. The centrifuge/wash step may be repeated several times. The sample is resuspended in a volume of a fixative and the sample then passes through the fluorescence flow cytometry instrument. A method and apparatus for performing flow automated analysis is described in co-owned U.S. patent application Ser. No. 08/283,379, now abandoned, which is incorporated herein by reference. It is within the scope of the present invention that microspheres can be utilized in the methods described herein, tagged or labeled, and employed for in vitro diagnostic applications. It also is within the scope of the present invention that other cells or particles, including bacteria, viruses, durocytes, etc., can be tagged or labeled with the PNAs or morpholino compound as described by the present invention and used in flow cytometric methods.

The present invention will now be described by way of examples, which are meant to illustrate, but not to limit, the spirit and scope of the invention.

EXAMPLES

Example 1

Synthesis of Peptides

All peptides were synthesized on an ABI Peptide Synthesizer, Model 431A, using FMOC chemistry, standard cycles and DCC-HOBt activation. Cleavage and deprotection conditions were as follows: the resin was added to 20 ml trifluoroacetic acid, 0.3 ml water, 0.2 ml ethanedithiol. 0.2 ml thioanisole and 100 mg phenol and stirred at room temperature for 1.5 hours. The resin then was filtered by suction and the peptide was obtained by precipitation of the TFA solution with ether followed by filtration. Each peptide was purified via reversed-phase preparative HPLC using a water/acetonitrile/0.1% TFA gradient and lyophilized. The product was confirmed by mass spectrometry.

Disulfide bond formation was accomplished using autooxidation conditions, as follows. The peptide was dissolved in a minimum amount of DMSO (approximately 10 ml) before adding buffer (0.1M Tris, pH 6.2) to a concentration of 0.3–0.8 mg/ml. The reaction was monitored by HPLC until complete formation of the disulfide bond, followed by reverse-phase preparative HPLC using a water/acetonitrile/ 0.1% TFA gradient and lyophilization. The product then was confirmed by mass spectrometry. All peptides contained a disulfide loop formed between the two cysteine (C) residues.

Example 2

EIA

A. Sample Procurement. The subtype-O samples "M" and "E" belonged to the original French panel of nine confirmed subtype-O samples; they are the same as samples #7 and #2 respectively (I. Loussert-Ajaka et al. *The Lancet* 343: 1393–1394 (1994)). Samples DUR, FAN and MAA were other subtype-O samples from the French Government.

Samples #2901 and HA112 were respectively obtained from Professors Lutz Gürtler of Munich, and Hartmut Hampl of Berlin, Germany. Samples #193, #267, #341, and #655 were obtained from Equatorial Guinea and have been PCR-confirmed to be true subtype-O samples.

B. EIA. The synthetic peptides were first dissolved in 0.1M morpholinoethane sulfonic acid (MES) buffer pH 5.5 to a concentration of 20 µM. For the coating step, 200 µL of various dilutions (0 to 5 fold) of the 20 µM solutions (in 0.1M MES buffer, pH 5.5) of each peptide were added to wells of Microtiter™ (Dynatech Immunolon 4 polystyrene) plates. After overnight incubation at room temperature, the plates were washed with a wash solution comprising 0.5% non-fat dry milk in TBST (Tris Buffer Saline, 0.01M Tris, 0.15M NaCl, 0.05% Tween-20®, pH 8). The blocking step required addition of 300 µL of a 10% non-fat dry milk in TBST solution to each well followed by a one-hour incubation at room temperature. Plates were then washed with the wash solution, before 150 μL of serum/plasma samples diluted 150-fold in 10% milk-TBST were added to each well. After a two-hour incubation at room temperature, the plates were washed again with the wash solution, and then to each well 100 μL of a 16,000 fold dilution of conjugate (goat anti-human IgG-horseradish peroxidase (HRPO), 1 mg/ml, Kirkegaard & Perry Laboratories, Inc., Gaithersburg, Md.) in 10% non-fat dry milk-TBST was added. Following a one-hour incubation, the plates were washed with the wash solution. Color development was achieved with the addition to each well of 100 μL of a solution of o-phenylene diamine (OPD) in hydrogen peroxide, and a ten-minute incubation. The color development reaction was quenched with 100 μL of 1N sulfuric acid and the absorbance determined with a Dynatech MR5000 plate reader at 490 nm and 630 nm wavelengths. The relative intensities of $A_{490}-A_{630}$ of the wells were proportional to the efficacy with which a particular peptide reacted with a particular serum/plasma sample.

Example 3

Comparative Analysis of the S to K Substitution and the T to Y Substitution

This example demonstrates the importance of the S to K substitution (SEQUENCE I.D. NO. 2) in the detection of some HIV-1 subtype-O samples (#2901, #267, and #655), the importance of the T to Y substitution (SEQUENCE I.D. NO. 3) in the detection of some other HIV-1 subtype-O samples (#193, "E", and HA112), and that both SEQUENCE I.D. NO. 2 and SEQUENCE I.D. NO. 3 were in general superior in performance to SEQUENCE I.D. NO. 1.

The assay was performed as described in Example 2. Please note that the peptide concentration used for coating the wells was 20 μM and the dilutions of the serum/plasma samples were: 150 fold for #193, #267, #341, #655, HA112 and DUR; 450 fold for #2901, samnples "E", and FAN; 750 fold for sample MAA; and 1500 fold for sample "M". Confirmed negative human HIV samples were used as the negative controls for this study.

The absorbance values reported in Tables 1, 2 and 3 were calculated as $A_{490}-A_{630}$.

TABLE 1

|  | SEQ I.D. 1 | SEQ I.D. 2 | SEQ I.D. 3 |
|---|---|---|---|
| Negative Control | 0.008 | 0.010 | 0.009 |
| Sample #193 | 1.180 | 1.116 | ≧2.5 |
| Sample #267 | 0.336 | 0.691 | 0.260 |
| Sample #341 | 0.365 | 1.635 | 1.384 |
| Sample #655 | 0.108 | 0.223 | 0.129 |

TABLE 2

|  | SEQ I.D. 1 | SEQ I.D. 2 | SEQ I.D. 3 |
|---|---|---|---|
| Negative Control | 0.014 | 0.008 | 0.010 |
| Sample "M" | 2.111 | ≧2.5 | ≧2.5 |
| Sample "E" | 0.051 | 0.144 | 1.085 |
| Sample #2901 | 0.028 | 1.511 | 0.049 |
| Sample HA112 | 0.703 | 1.286 | 2.274 |

TABLE 3

|  | SEQ I.D. 1 | SEQ I.D. 2 | SEQ I.D. 3 |
|---|---|---|---|
| Negative Control | 0.007 | 0.006 | 0.005 |
| Sample DUR | 0.591 | 1.202 | 0.442 |
| Sample FAN | 0.355 | 1.316 | 0.575 |
| Sample MAA | 0.412 | 2.440 | 1.739 |

Example 4

Comparative Analysis of the S to K and T to Y Di-Substitution

This example demonstrated that the S to K and T to Y di-substituted peptide (SEQUENCE I.D. NO. 4) was markedly superior in performance to SEQUENCE I.D. NO. 1 in the detection of 10 out of a total of 11 subtype-O samples.

The assay was performed as described in Example 2. Please note that the peptide concentration used for coating the wells was 20 μM and the dilutions of the serum/plasma samples were: 150 fold for #193, #267, #341, #655, HA112 and DUR; 450 fold for #2901, samples "E", and FAN; 750 fold for sample MAA; and 1500 fold for sample "M". As described in Example 3, confirmed negative human HIV samples were used as the negative controls for this study.

The numbers reported in the Tables 4, 5 and 6 were absorbance values ($A_{490}-A_{630}$).

TABLE 4

|  | SEQ I.D. 1 | SEQ I.D. 4 |
|---|---|---|
| Negative Control | 0.008 | 0.014 |
| Sample #193 | 1.180 | ≧2.5 |
| Sample #267 | 0.336 | 1.059 |
| Sample #341 | 0.365 | ≧2.5 |
| Sample #655 | 0.108 | 0.289 |

TABLE 5

|  | SEQ I.D. 1 | SEQ I.D. 4 |
|---|---|---|
| Negative Control | 0.014 | 0.015 |
| Sample "M" | 2.111 | ≧2.5 |
| Sample "E" | 0.051 | ≧2.5 |
| Sample #2901 | 0.028 | 1.276 |
| Sample HA112 | 0.703 | ≧2.5 |

TABLE 6

|  | SEQ I.D. 1 | SEQ I.D. 4 |
|---|---|---|
| Netative Control | 0.007 | 0.005 |
| Sample DUR | 0.591 | 0.358 |
| Sample FAN | 0.355 | 0.624 |
| Sample MAA | 0.412 | 2.247 |

Example 5

Titration Studies

A. Experimental Protocol. The relative immunoreactivity for HIV synthetic peptides was measured using 96-well plates coated for 16 hrs at 4° C. with 100 μL of each of the following peptides prepared as described in Example 1: consensus B (SEQUENCE I.D. No. 1), B/O-7 (SEQUENCE I.D. No. 2), B/O-8 (SEQUENCE I.D. No. 3), and B/O-2

(SEQUENCE I.D. No. 4). The peptides were evaluated at the following concentrations: 500 µM, 50 µM, 5 µM, 0.5 µM, 0.05 µM, and 0.005 µM. The buffer used for the application of these peptides was 100 mM morpholinoethane sulfonic acid, pH 5.5. The peptide-coated wells were then washed three times with the wash buffer consisting of 8 mM sodium phosphate, 2 mM potassium phosphate, 140 mM sodium chloride, 10 mM potassium chloride, 0.05% tween 20, 0.1% bovine serum albumin, pH 7.4.

The wells were then blocked one hr at room temperature with 9% (w/v) Carnation® skim milk powder in phosphate buffered saline: 8 mM sodium phosphate, 2 mM potassium phosphate, 140 mM sodium chloride, 10 mM potassium chloride, pH 7.4. The wells were then washed 3 times with the wash buffer.

Human serum samples (#193, #267, #341, #655 and "M") were diluted 150-fold with 4.5% Carnation® skim milk powder (w/v) in PBS. One hundred µL of these samples were incubated in the wells at 37° C. for 1 hr. The wells were then washed 3 times with the wash buffer.

Antibody positive samples which contained the HIV antibody-peptide antigen complex, were detected using horseradish peroxidase conjugated to goat anti-human IgG. One hundred uL of HRPO-goat anti-human IgG conjugate, diluted 1:5000 in the wash buffer, was added to each well and incubated at room temperature for 1 hr. The wells were then washed 3 times with wash buffer and the concentration of HIV antibody estimated by absorbance readings at 405 nm after exposure of the wells to 100 µL of ABTS solution (2,2'-azinobis-[3-ethylbenzothizoline-6-sulfonic acid] diammonium salt) from Pierce.

Figure 1:
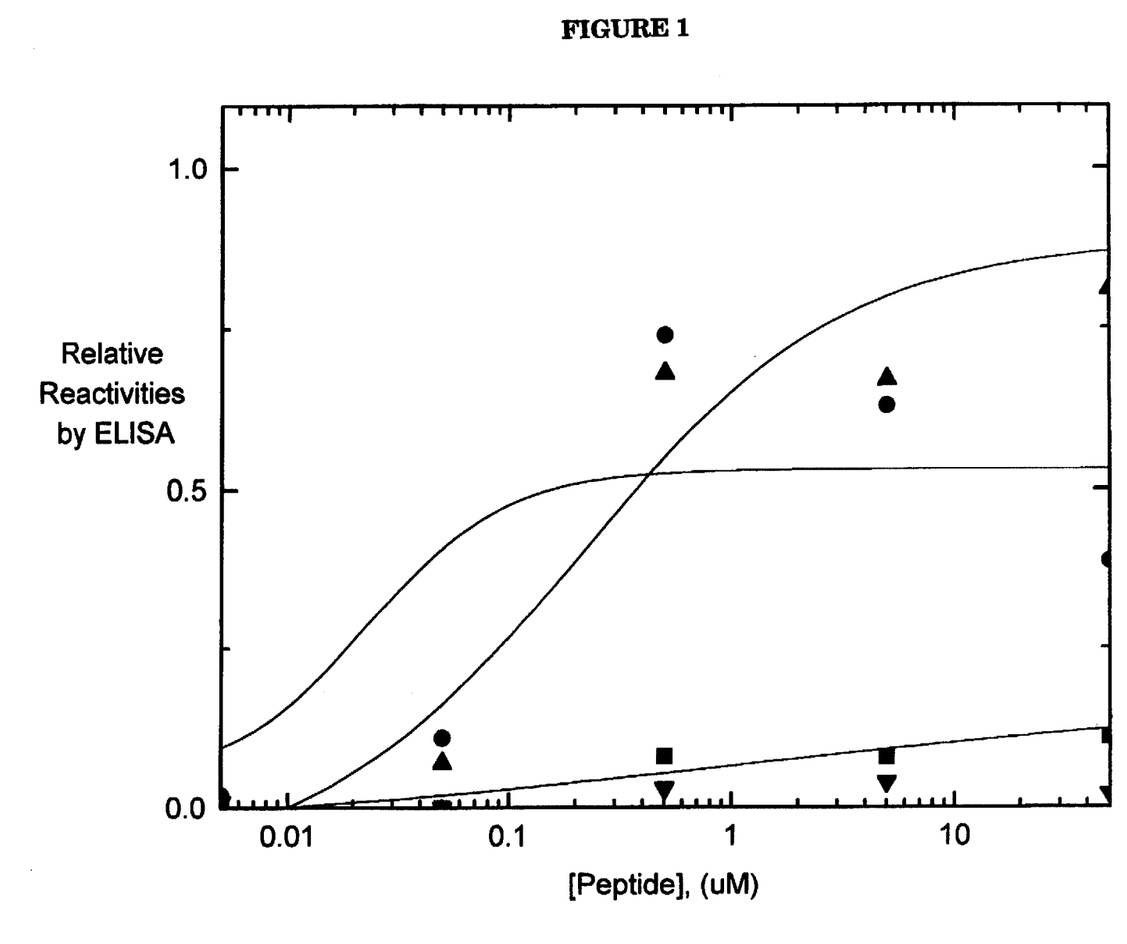
FIG. 1 shows the relative reactivities by ELISA of SEQUENCE I.D. No. 1 (▼) SEQUENCE I.D. No. 2 (■), 
SEQUENCE I.D. No. 3 (●) and SEQUENCE I.D. No. 4 (▲) for sample #193.
Figure 2:
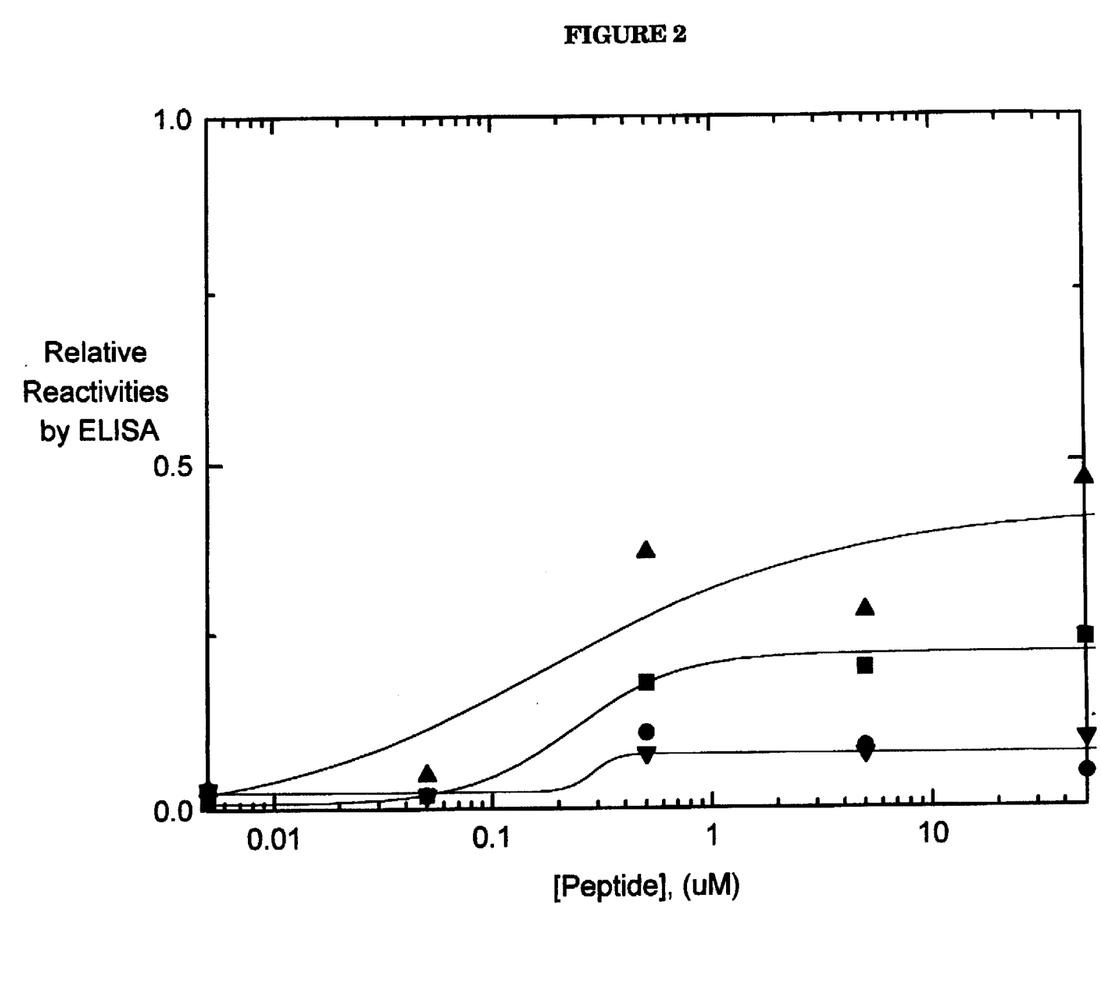
FIG. 2 shows the relative reactivities by ELISA of SEQUENCE I.D. No. 1 (▼) SEQUENCE I.D. No. 2 (■), SEQUENCE I.D. No. 3 (●) and SEQUENCE I.D. No. 4 (▲) for sample #267.
Figure 3:
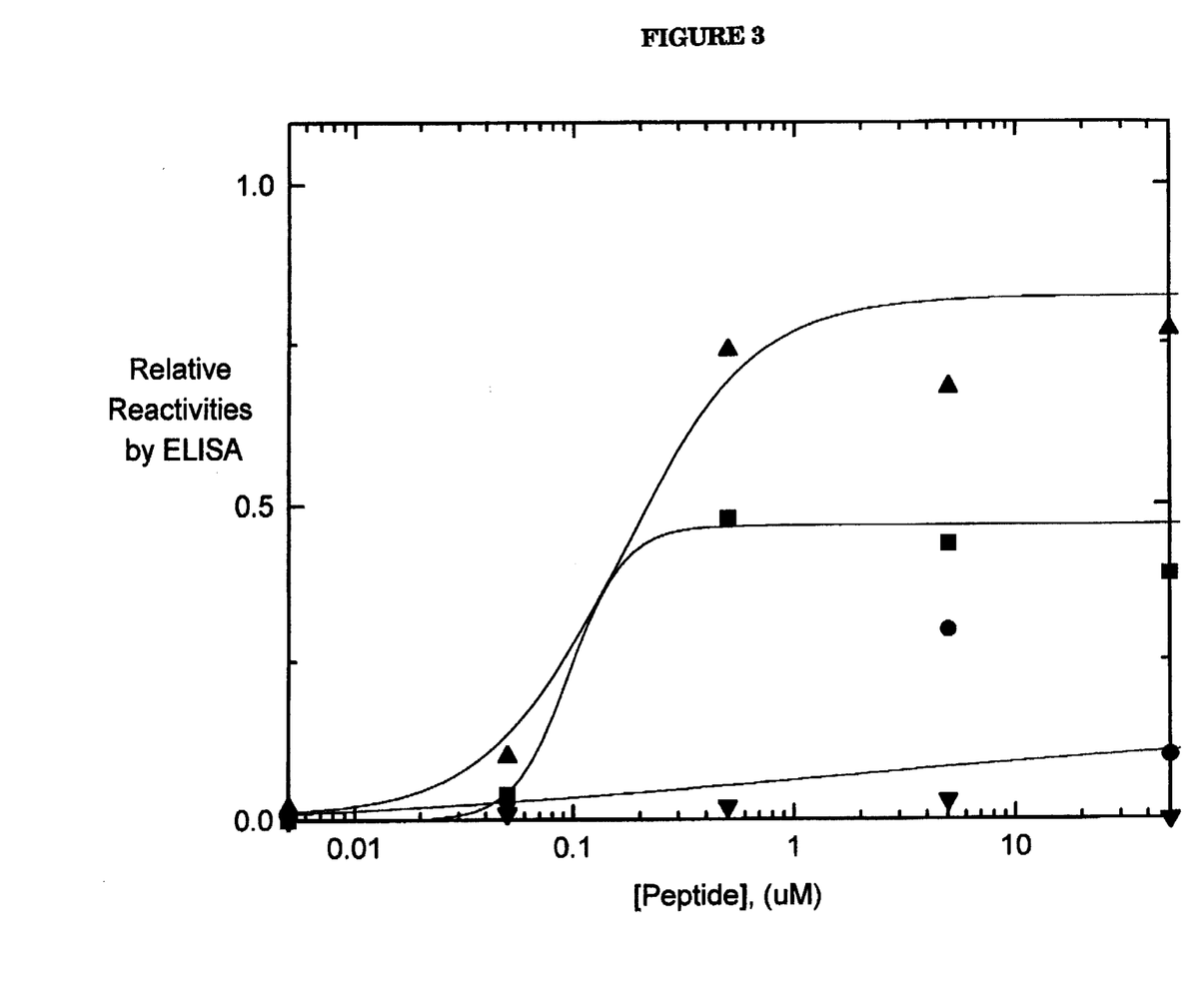
FIG. 3 shows the relative reactivities by ELISA of SEQUENCE I.D. No. 1 (▼) SEQUENCE I.D. No. 2 (■), SEQUENCE I.D. No. 3 (●) and SEQUENCE I.D. No. 4 (▲) for sample #341.
Figure 4:
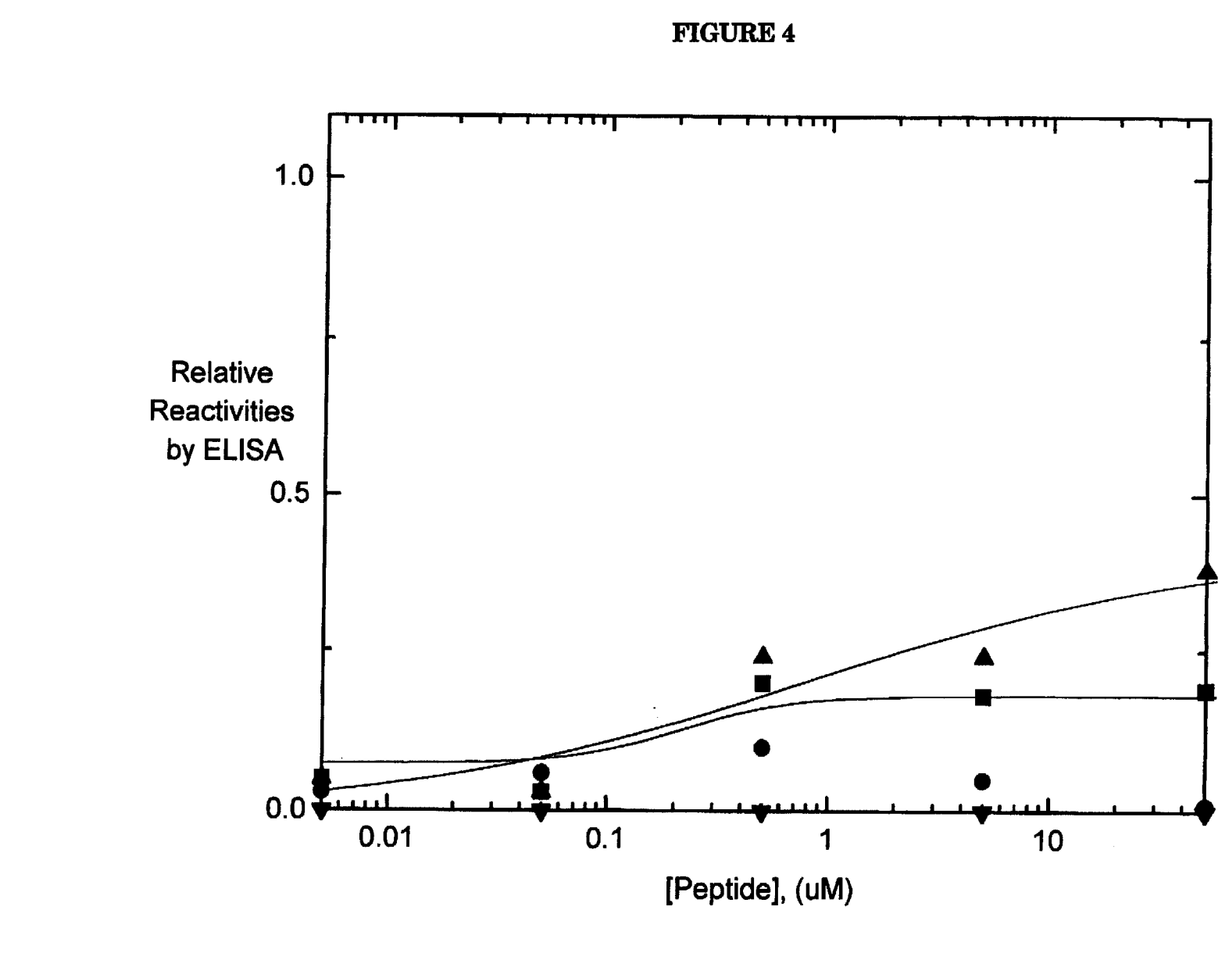
FIG. 4 shows the relative reactivities by ELISA of SEQUENCE I.D. No. 1 (▼) SEQUENCE I.D. No. 2 (■), SEQUENCE I.D. No. 3 (●) and SEQUENCE I.D. No. 4 (▲) for sample #655.
Figure 5:
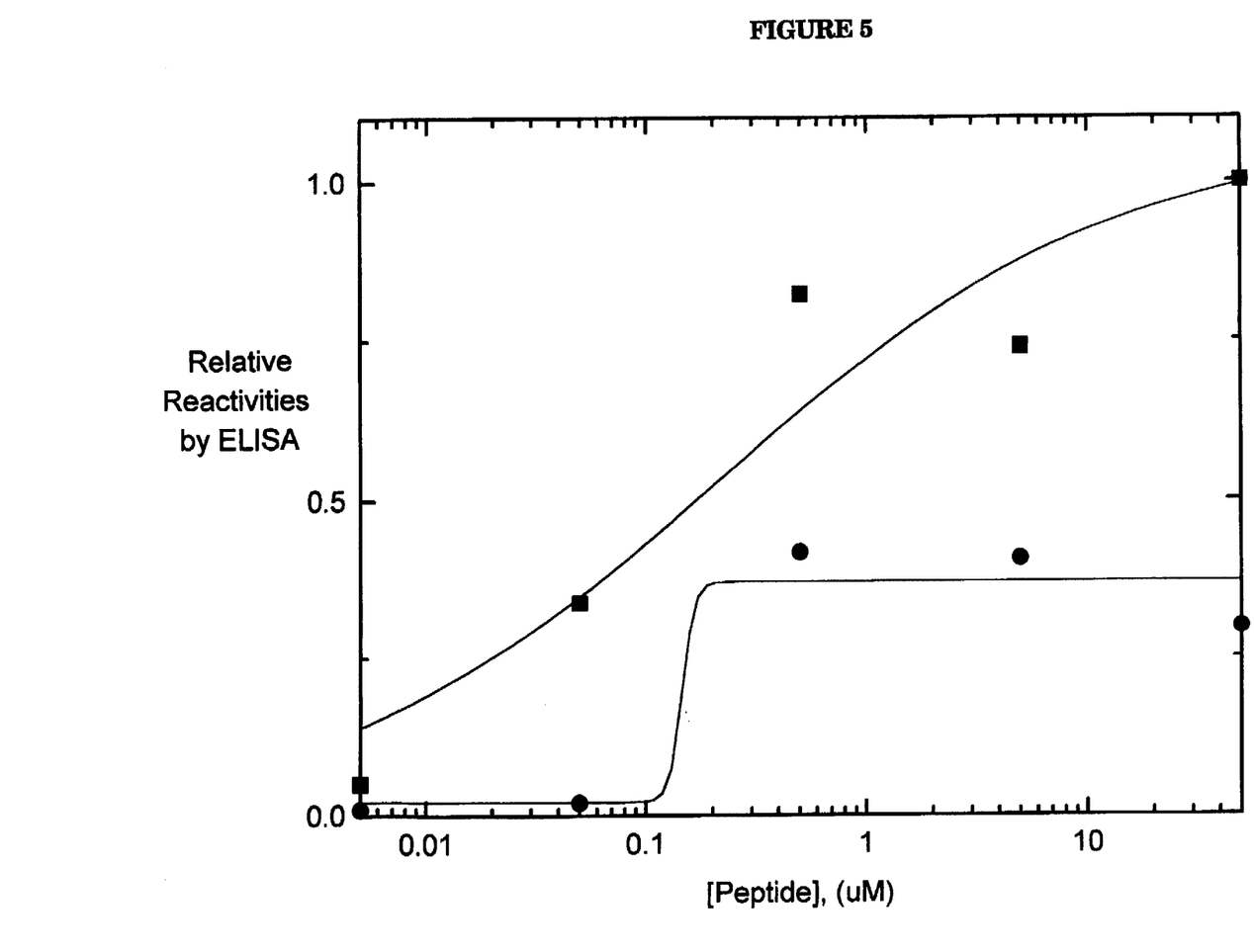
FIG. 5 shows the relative reactivities by ELISA of SEQUENCE I.D. No. 2 (■) and SEQUENCE I.D. No. 3 (●) for sample M.

B. Data Analysis. The absorbance readings at 405 nm were normalized to SEQUENCE I.D. No. 4 and the relative reactivities were plotted against the log of the peptide concentration used to coat the wells. The data were fit to an equation describing a sigmoidal curve as found in the Origin program written by Microcal Inc.

$$y=(A_1-A_2)/\{1+(x/x_0)^p\}+A_2$$

where $x_o$ is the center of the curve, p is the rate, $A_1$ is y initial, and $A_2$ is y final.

C. Results. FIGS. 1, 2, 3 and 4 illustrate that the 20 µm peptide concentration is sufficient to generate a saturation signal, thus validating the previous data in Examples 3 and 4.

---

We claim:

1. A polypeptide having a point mutation in the HIV-1 sub-type B IDR at position 604.

2. The polypeptide of claim 1 wherein said point mutation at position 604 is a lysine (K).

3. The polypeptide of claim 2 as identified by SEQUENCE I.D. No. 2.

4. A polypeptide having a point mutation in the HIV-1 sub-type B IDR at position 610.

5. The polypeptide of claim 4 wherein said point mutation at position 610 is a tyrosine (Y).

6. The polypeptide of claim 5 as identified by SEQUENCE I.D. No. 3.

7. A polypeptide having two single point mutations in the HIV-1 sub-type B IDR at positions 604 and 610.

8. The polypeptide of claim 7 wherein said point mutation at position 604 is a lysine (K) and the point mutation at position 610 is a tyrosine (Y).

9. The polypeptide of claim 8 as identified by SEQUENCE I.D. No. 4.

10. Polypeptide SEQUENCE I.D. No. 2.

11. Polypeptide SEQUENCE I.D. No. 3.

12. Polypeptide SEQUENCE I.D. No. 4.

13. An immunoassay to detect the presence of HIV antibodies in a test sample, comprising:

a) contacting said test sample with a solid phase to which has been attached an HIV-1 polypeptide having a point mutation between positions 593 and 611 to form a first mixture, and incubating said first mixture for a time and for conditions sufficient to form polypeptide/antibody complexes;

b) contacting said polypeptide/antibody complexes with an indicator reagent comprising a member of a specific binding pair attached to a signal generating compound capable of generating a measureable signal to form a second mixture, and incubating said second mixture for a time and for conditions sufficient to form polypeptide/antibody/indicator reagent complexes; and c) determing the presence of HIV antibodies in said test sample by detecting the measureable signal.

14. The immunoassay of claim 13 wherein said point mutation is at position 604.

15. The immunoassay of claim 13 wherein said point mutation is at position 610.

16. The immunoassay of claim 13 wherein said point mutations are at positions 604 and 610.

17. The immunoassay of claim 13 wherein said solid phase is selected from the group consisting of the walls of wells of a reaction tray, test tubes, polystyrene beads, magnetic beads, nitrocellulose strips, membranes, microparticles such as latex particles, red blood cells, and duracytes.

18. The immunoassay of claim 13 wherein said indicator reagent comprises a signal generating compound selected from the group consisting of chromogens, enzymes, luminescent compounds, chemilumninescent compounds, radioactive elements, and direct visual labels.

19. The immunoassay of claim 13 wherein said specific binding pair member of said indicator reagent is anti-human IgG.

20. In an immunoassay for detecting HIV antibody in a test sample comprising contacting said test sample with an HIV-1 polypeptide and detecting the presence of said antibody, wherein the improvement comprises utilizing a polypeptide having at least one point mutation between positions 593 and 611 of the HIV-1 gp 160 sequence.

21. A dignostic test kit capable of detecting HIV antibodies comprising a container containing a polypeptide having a sequence selected from the group consisting of SEQUENCE I.D. No. 2, SEQUENCE No. 3 and SEQUENCE No. 4.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Lys Asp Gln Gln Leu Leu Gly Ile Trp Gly Cys Ser Gly Lys Leu Ile
1               5                   10                  15

Cys Thr Thr
```

( 2 ) INFORMATION FOR SEQ ID NO:2:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

```
Lys Asp Gln Gln Leu Leu Gly Ile Trp Gly Cys Lys Gly Lys Leu Ile
1               5                   10                  15

Cys Thr Thr
```

( 2 ) INFORMATION FOR SEQ ID NO:3:

( i ) SEQUENCE CHARACTERISTICS:
( A ) LENGTH: 19 amino acids
( B ) TYPE: amino acid 
```
         ( C ) STRANDEDNESS: single
         ( D ) TOPOLOGY: linear ( i i ) MOLECULE TYPE: protein ( x i ) SEQUENCE DESCRIPTION: SEQ ID NO:3:

Lys Asp Gln Gln Leu Leu Gly Ile Trp Gly Cys Ser Gly Lys Leu Ile
1                 5                  10                  15

Cys Tyr Thr ( 2 ) INFORMATION FOR SEQ ID NO:4:

( i ) SEQUENCE CHARACTERISTICS:
             ( A ) LENGTH: 19 amino acids
             ( B ) TYPE: amino acid
             ( C ) STRANDEDNESS: single
             ( D ) TOPOLOGY: linear ( i i ) MOLECULE TYPE: protein ( x i ) SEQUENCE DESCRIPTION: SEQ ID NO:4:

Lys Asp Gln Gln Leu Leu Gly Ile Trp Gly Cys Lys Gly Lys Leu Ile
1                 5                  10                  15

Cys Tyr Thr
```